United States Patent [19]

Jörn

[11] Patent Number: 4,616,508

[45] Date of Patent: Oct. 14, 1986

[54] METHOD AND APPARATUS FOR PRODUCING A TEST PIECE OF MOLDING COMPOUND USEFUL IN MEASURING PROPERTIES THEREOF

[75] Inventor: Alfred Jörn, Bibern, Switzerland

[73] Assignee: Georg Fischer Aktiengesellschaft, Schaffhausen, Switzerland

[21] Appl. No.: 579,661

[22] Filed: Feb. 13, 1984

[30] Foreign Application Priority Data

Feb. 28, 1983 [CH] Switzerland ............... 1093/83

[51] Int. Cl.4 .......................................... G01N 3/08
[52] U.S. Cl. .................................. 73/823; 73/825; 73/818
[58] Field of Search ............... 73/823, 825, 818, 821, 73/798, 774, 777

[56] References Cited

U.S. PATENT DOCUMENTS

| | | | |
|---|---|---|---|
| 2,447,586 | 8/1948 | Marshall | 73/818 |
| 2,791,120 | 5/1957 | Dietert et al. | 73/821 |
| 3,065,625 | 11/1962 | Brown | 73/798 |
| 3,638,478 | 2/1972 | Dietert et al. | 73/823 |

FOREIGN PATENT DOCUMENTS 8118255 10/1981 Fed. Rep. of Germany .

| | | |
|---|---|---|
| 665281 | 1/1952 | United Kingdom . |
| 795668 | 5/1958 | United Kingdom . |
| 1127647 | 9/1968 | United Kingdom . |
| 1173235 | 12/1969 | United Kingdom . |
| 1179350 | 1/1970 | United Kingdom . |
| 1216397 | 12/1970 | United Kingdom . |
| 1374113 | 11/1974 | United Kingdom . |
| 1378092 | 12/1974 | United Kingdom . |
| 1417799 | 12/1975 | United Kingdom . |
| 1445736 | 8/1976 | United Kingdom . |
| 1551954 | 9/1979 | United Kingdom . |
| 204503 | 4/1968 | U.S.S.R. ............... 73/823 |

Primary Examiner—Stewart J. Levy
Assistant Examiner—John E. Chapman, Jr.
Attorney, Agent, or Firm—Toren, McGeady, Stanger, Goldberg & Kiel

[57] ABSTRACT

A specific measured volume of a molding compound is placed within a cavity having a certain geometry and a compacting pressure is applied thereto until a predetermined measured pressure is reached on a side of said molding compound opposite the side where the pressure is applied in order to produce a test piece, with the volume of the test piece at the point at whcih the predetermined pressure is reached being determined so that the test piece may be subsequently used for determining other mechanical properties of the compound.

11 Claims, 2 Drawing Figures

METHOD AND APPARATUS FOR PRODUCING A TEST PIECE OF MOLDING COMPOUND USEFUL IN MEASURING PROPERTIES THEREOF

The present invention relates generally to measurement of one or more properties of a molding compound and more particularly to a method and apparatus for producing a test piece of said molding compound useful in measurement of the properties thereof.

In methods known hitherto for measurement of molding compound properties and particularly in standardized for producing test pieces required for such measurement, it has been found that there has been a failure to meet the requirements of a measurement-dependent action on the molding compound composition as required for the production of exact castings in quantity production.

Accordingly, the present invention is directed toward provision of a method of the type initially mentioned which enables exact measurement of molding compound properties in order to effect, with the determined test values, automatic regulation of the molding compound preparation to achieve constant quality of the molding compound.

SUMMARY OF THE INVENTION

In accordance with the method of the present invention, a test piece of molding compound useful for measurement of the properties of the molding compound is produced utilizing the steps of providing a specific measured volume of the molding compound within a cavity having a certain geometry, applying compaction means to the molding compound in said cavity, measuring the pressure on the measured volume of compound at a surface thereof opposite the side to which the compaction means is applied, and compacting said volume of molding compound in the cavity to a certain compaction energy per ultimate compaction volume corresponding to a fixed measured pressure at said opposite surface of said volume of the molding compound.

Furthermore, the invention may be described as apparatus for producing a test piece of molding compound in accordance with the method described above comprising means defining a cavity having a certain geometry within which a specific measured volume of the molding compound may be provided, compaction means for applying a compaction pressure to said compound from one side of said cavity, means for measuring the pressure on the compound on a side of the cavity opposite said one side, and means for measuring the distance moved by the compaction means.

By producing a molding compound test piece from a certain quantity of molding compound in a cavity having a certain geometry and volume by compacting the compound to a certain compaction energy per ultimate compaction volume corresponding to a fixed measured pressure at the surface opposite the compaction means, it is ensured that all the produced test pieces are produced with the same degree of compaction independently of the moisture of the molding compound, although the final volume is different depending on the moisture content of the molding compound.

The same degree of compaction of all test pieces ensures more exact measurement results in the different measuring methods on the test pieces than was possible hitherto.

With the apparatus of the invention, simple production of molding compound test pieces may be ensured with all the test pieces having the same degree of compaction, the apparatus having the special feature of simple construction and operational safety.

The various features of novelty which characterize the invention are pointed out with particularity in the claims annexed to and forming a part of this disclosure. For a better understanding of the invention, its operating advantages and specific objects attained by its use, reference should be had to the accompanying drawing and descriptive matter in which there are illustrated and described preferred embodiments of the invention.

DETAILED DESCRIPTION OF THE PREFERRED EMBODIMENTS

Figure 1:
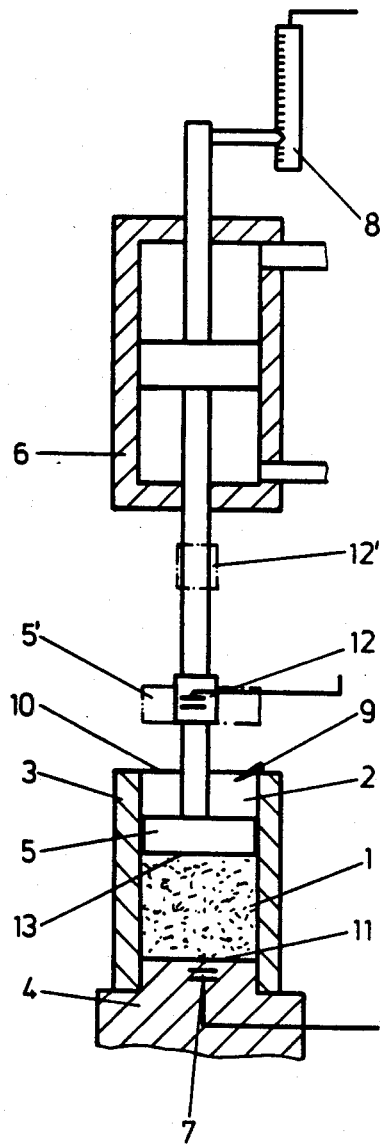
FIG. 1 is a schematic sectional view showing the apparatus required for the production of a test piece in accordance with the invention and useful in performance of the invention.

Referring now to the drawing, there is shown apparatus in accordance with the present invention for producing a test piece of molding compound, the apparatus comprising a cylindrical sleeve 3 and a bottom member 4 defining a cavity 2 within which a specific volume of molding compound 1 may be inserted. The molding compound from which the test piece is to be formed may be inserted in the direction of the arrow 9 and, by means of a scraping operation on the upper edge of the cylinder 3, a constant volume of the molding compound extending up to a top edge 10 of the sleeve 3 may be obtained.

The apparatus also includes a ram 5 which is part of a compaction means 6 which may consist preferably of a hydraulic or pneumatic piston-cylinder unit. Of course, when the molding compound is to be inserted into the cavity 2, the ram 5 is raised to a position indicated in dash-dot form at 5'.

In the bottom member 4 of the apparatus there is provided a force- or pressure measuring device 7 which generates an electrical or hydraulic signal indicative of the pressure at a surface 11 of the molding compound 1 which is opposite an upper surface 13 thereof at which the ram 5 is applied.

Also provided is a distance measuring device 8 which provides an indication of the distance which is moved by the ram 5 of the compaction means 6.

In the performance of the method of the present invention, with the ram 5 pulled out to the position 5', molding compound is filled into the cavity 2, for example from a molding compound processing installation, in the direction of the arrow 9 in such a manner that after the scraping operation is performed, a constant volume will be provided extending up to the top edge 10.

The ram 5 is then pushed downwardly by means of the piston-cylinder unit of the compaction means 6 and the molding compound is compacted until, at the surface 11 of the molding compound test piece abutting the bottom 4, there has been reached a fixed compaction force or pressure. This force is measured continuously by means of the force measuring device 7 and the ram is relieved of pressure after a fixed force or pressure has been achieved.

If the compactability of the molding compound is to be measured thereon, this is done during the compaction of the test piece. At a certain adjusted pressure at the ram, for example at 10 kg/cm$^2$, the compaction path starting from the top edge 10 of the sleeve 3 is measured by means of the distance measuring device 8, this being a measure of the compactability.

After this measurement, the pressing force is varied until, at the surface 11, the value adjusted at the force measuring device 7 is reached.

The test piece thus produced may then be used for additional measurements of the properties of the molding compound such as gas permeability, shearing, compressive or tensile strength, and for this purpose the test piece 1 is removed from the cavity, either partially or entirely.

In addition to the force measuring device 7 at the bottom member 4, another force measuring device 12 may be provided at the compaction or pressure means 6 or respectively at the ram 5, as will be seen from the drawing. Of course, the reference numeral 12' indicates the position of this other force measuring device when the ram is in the raised position. Thus, the force or respectively the compaction pressure can be measured during compaction or only at the end of the compacting process at the lower surface 11 and at the upper surface 13 of the test piece 1, it being possible also to evaluate both values or respectively the difference therebetween.

Figure 2:
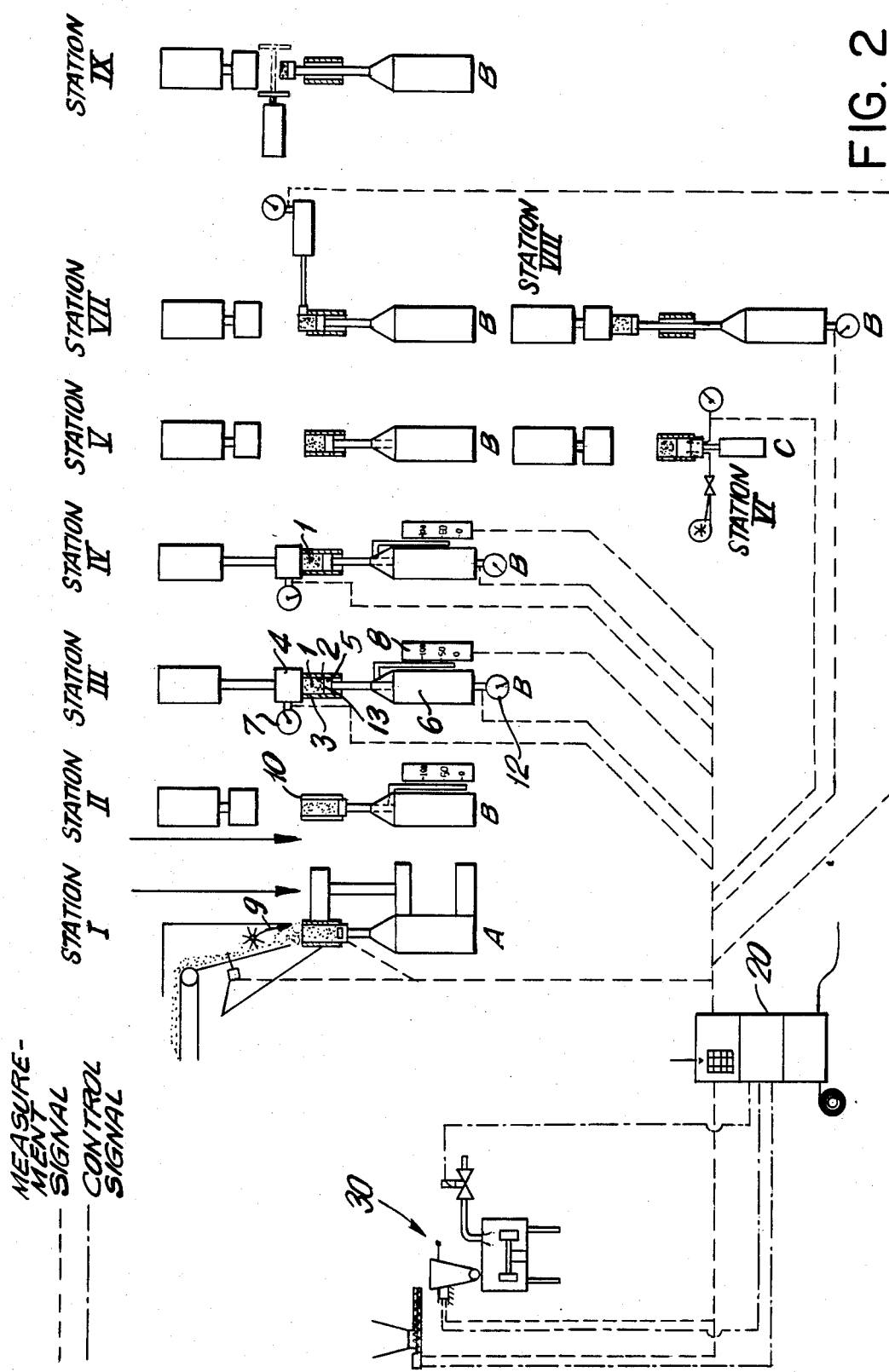
FIG. 2 is a schematic diagram of a system embodying the present invention.

The measuring apparatus can be advantageously used for automatic regulation of a molding compound processing installation, as exemplified by the system of FIG. 2, the various measured values being stored in a computer, processed, and transferred in regulating equipment into regulating or control signals for valves or other proportioning devices for the supply of water, bonding clay and other additives to the molding compound.

In FIG. 2, there is shown a measuring device which is in actuating connection by means of a control 20 with a molding compound processing apparatus 30.

In Station I which includes the apparatus 30, there occurs the filling process of the cavity 2 with loose molding compound from the molding compound processing apparatus. Hereby, there also occurs a temperature measurement.

Station II shows the filling of the cavity 2.

Station III shows the compression process, whereby, in the course of this process, the compressibility of the molding compound with a predetermined force of the compression means 6 (measured with the measuring device 12) is determined by measuring the compression travel by means of the measuring device.

Additionally, it is also possible to measure the compressive force at the base 4 by means of the measuring device 7.

Station IV shows the finished compressed test specimen 1, whose fabrication according to the invention at a predetermined pressure at the base 4 as measured with the measuring device 7 is being finished.

Station V shows the test specimen lifted off from the base.

Station VI shows the measurement of gas-permeability of a test specimen.

Station VII shows the measurement of the shearing strength of the partially pushed out test specimen by means of a transversely displaceable shearing device.

Station VIII shows the measurement of the compressive strength of the test specimen.

Station IX shows the removal of the test specimen and the cleaning of the cavity.

Apart from that, the actuating connection of the measuring device by means of a control with the molding compound processing apparatus is shown in the drawing. Measured values are automatically recorded and are transformed into control or regulating signals. In the system shown in FIG. 2, there are generated signals for automatically controlling or regulating the apportioning of mixture components that are necessary for preparing the molding compound. The control or regulating signals are utilized for correcting the control signals which, in the region of molding compound preparation, are supplied by other measuring devices. The signals are utilized for recording a quantity of apportioned mixing components.

In accordance with a further aspect of the method of the invention, during the compacting process, at a certain force exerted by the compaction means, the compactability is measured with reference to the volume decrease. Measuring of the compactability during or at the end of the compaction process in accordance with this feature of the invention serves to determine the degree of wetting of the molding compound.

In accordance with a further feature of the invention, additionally the pressing force on the surface bearing against the compaction means may be measured by utilization of the force measuring device 12 and a test signal produced from the two measured pressing forces from both the devices 7 and 12. This permits evaluating both pressing force test data, for example by difference or quotient formation.

In accordance with a further feature of the invention, the test piece, either partially or wholly outside of the cavity, may be exposed to compressive, shear, or tensile load and the force required for rupture of the test piece, with or without respective deformation of the test piece, is measured. By this measuring method, and particularly by measuring the shear strength as an expression of the bonding clay content, the required content of bonding clay and additives can be determined.

Furthermore, filling of the cavity may be performed automatically by apportioning means so that during the filling the temperature is measured automatically so that the test cycle, removal of the molding compound test piece from the cavity, and cleaning thereof are performed automatically. As a result, automatic regulation of the molding compound processing may be performed, and measured values are automatically recorded and are transformed into control or regulating signals. The signals may then be utilized to automatically control or regulate the apportioning of the mixture components that are necessary for preparing the molding compound.

The signals are then utilized for correcting the control signals which in the region of the molding compound preparation are supplied by other measuring devices. For example, a moldability controller may be utilized for the molding compound processing.

The signals are utilized for recording the quantity of apportioned mixing components and by means of the test signals, the consumption of the apportioned mixture components may be determed whereby stock keeping and cost determination will be facilitated.

Thus, it will be seen that the invention provides for the measurement of molding compound properties by providing a molding compound test piece which is produced in a cavity 2 by means of compaction means 5, 6. By means of the ram 5, a pressure or pressing force is exerted on the molding compound which is of a level until, at the bottom 4 of the sleeve, a fixed pressure is reached which is measured by the pressure measuring device 7.

While specific embodiments of the invention have been shown and described in detail to illustrate the application of the inventive principles, it will be understood that the invention may be embodied otherwise without departing from such principles.

What is claimed is:

1. A method for measuring mechanical properties of a molding compound including producing a test piece of said molding compound useful for measurement of said properties comprising the steps of providing a specific measured volume of said molding compound within a cavity having a certain geometry, applying compaction means to a surface of said molding compound from one side of said cavity, measuring the pressure on said measured volume of compound directly at a surface thereof on a side of said cavity opposite said one side from which said compaction means is applied and compacting said volume of said molding compound in said cavity to a certain compaction energy per ultimate compaction volume corresponding to a fixed measured pressure sensed at said opposite surface of said volume.

2. A method according to claim 1 wherein during said compaction of said volume at a certain pressure exerted by said compaction means, the compactability is measured with reference to the decrease in volume of said compound.

3. A method according to claim 1 wherein in addition to measuring the pressure on said opposite surface, there is also measured the pressure on the surface against which said compaction means is applied with a test signal being produced from said two measured pressures.

4. A method according to claim 1 wherein the gas permeability of the test piece thus compacted is measured.

5. A method according to claim 1 wherein filling of said cavity with said measured volume of said molding compound is performed automatically by apportioning means, wherein during said filling the temperature is automatically measured, wherein the test cycle, the removal of the molding compound test piece from the cavity and cleaning thereof are performed automatically.

6. A method according to claim 5 wherein measured values are automatically recorded and are transformed into control or regulating signals.

7. A method according to claim 6 wherein there are generated signals for automatically controlling or regulating the apportioning of mixture components that are necessary for preparing said molding compound.

8. A method according to claim 6 wherein said signals are utilized for correcting the control signals which in the region of molding compound preparation are supplied by other measuring devices.

9. A method according to claim 7 wherein said signals are utilized for recording the quantity of apportioned mixing components.

10. Apparatus for producing a test piece of molding compound useful for measurement of the properties of said compound by compressing said compound to a specified pressure at a particular volume comprising means defining a cavity having a certain geometry within which a specific measured volume of said molding compound may be provided, compaction means for applying a compaction pressure to said compound from one side of said cavity, sensing means for measuring the pressure on said compound on a side of said cavity opposite said one side, means for measuring the distance moved by said compaction means, said sensing means being located to measure the pressure applied by said compaction means directly at the surface of said molding compound on a side of said cavity opposite said one side.

11. Apparatus according to claim 10, further comprising additional pressure measuring means arranged to measure the pressure on said molding compound at said one side of said cavity where said compaction means is applied.

* * * * *